United States Patent [19]

Sawruk

[11] Patent Number: 4,623,355

[45] Date of Patent: Nov. 18, 1986

[54] PROSTHETIC AXON

[76] Inventor: Stephen D. Sawruk, 11 High St., Nutley, N.J. 07110

[21] Appl. No.: 766,792

[22] Filed: Aug. 19, 1985

Related U.S. Application Data

[63] Continuation-in-part of Ser. No. 590,561, Mar. 16, 1984, abandoned.

[51] Int. Cl.⁴ ............................................. A61F 2/00
[52] U.S. Cl. ..................................... 623/66; 128/1 R; 128/642; 128/334 R
[58] Field of Search ............................ 623/66, 24, 25; 128/1 R, 334 R, 346, 419 R, 784, 785, 642, 419 C

[56] References Cited

U.S. PATENT DOCUMENTS

| | | | |
|---|---|---|---|
| 3,786,817 | 1/1974 | Palma | 128/334 R |
| 3,833,002 | 9/1974 | Palma | 128/334 R |
| 3,955,560 | 5/1976 | Stein et al. | 623/66 X |
| 4,011,861 | 3/1977 | Enger | 128/419 C X |
| 4,026,300 | 5/1977 | DeLuca et al. | 623/24 X |
| 4,281,668 | 8/1981 | Richter et al. | 128/784 |

FOREIGN PATENT DOCUMENTS 2124495  2/1984  United Kingdom ............ 128/419 R Primary Examiner—Richard J. Apley
Assistant Examiner—Alan W. Cannon
Attorney, Agent, or Firm—Melvin K. Silverman; Joseph A. Giampapa

[57] ABSTRACT

A prosthetic axon for electrically bridging damaged nerve fibers constitutes a semi-conductive disc having therein pores substantially parallel to the polar axis of the disc, the pores having an interior coating of electrically conductive material extending substantially from the top to bottom surfaces of the disc, in which respective sides of the damaged nerve fibers are conductively secured to opposite sides of opposite pore ends of the conductive interior coating of the pores. The disc is embedded within a protein gel which is in electrical contact with both the conductive pore coating and the damaged nerve fibers.

17 Claims, 5 Drawing Figures

PROSTHETIC AXON

REFERENCE TO RELATED APPLICATION

This is a Continuation-In-Part of application Ser. No. 590,561 filed March 16, 1984 now abandoned.

BACKGROUND OF THE INVENTION

The present invention relates to means for effecting an electrical connection between normally continuous nerve fiber that has been damaged or injured as to interrupt or interfere with the normal conduction of biological electrical impulses therethrough.

The need for conducting bio-electrical signals across an injured or damaged group of nerve fibers has constituted one of the most long-standing and difficult problems in the treatment of neurological injury. Prior technical activity in the present area has, for the most part, related to the use of extracorporeal devices, utilizing gross electrodes, in order to attempt to bridge breaks in nerve fibers. These efforts, as well as efforts to deal with the problem at the micro-electronic level, have not been successful. Also, methods at implanting microelectrodes and related devices into nerve fibers has met with only limited success. Examples of such efforts appear in U.S. Pat. No. 3,955,565 to Stein, entitled Implantable Neural Electrodes; No. 4,281,668 to Richter, entitled Implantable Electrode; and No. 4,307,472 to Morris, entitled Prosthetic Device With Rigid Implantable Member Having Bonded Porous Coating.

United Kingdom Patent No. 2,124,495 to Kuzma, entitled Prosthetic Package, discloses a ceramic disc used in reconstructive neurology of the human ear.

Other prior art methods have related to bio-electronic techniques for the stimulation of cell growth following injury (see Stein above). Some prior art efforts have also related to the chemistry of in vitro implantation of an electronic device (see Morris and Kuzma above). There is, however, nothing in the prior art that constitutes a complete prosthesis for a damaged segment of nerve fibers. It is toward the solution of this basic neurological problem that the present invention is directed.

Applicable bibliography in this area includes the following references:
1. Gray's Anatomy, Goss, 29th Edition.
2. Developmental Anatomy, Arey, 7th Edition.
3. The Neurologic Examiner, Demyer, 2nd Edition.
4. Correlative Neuroanatomy and Functional Neurology, Lange, 1975
5. Medical Physiology, Guyton, 4th Edition The instant invention is believed to be properly classified in U.S. Class 3, Subclass 1; and U.S. Class 128, Subclasses 1, 334, 419 and 784.

SUMMARY OF THE INVENTION

The present invention comprises a semi-conductive disc of silicon provided with a plurality of pores, which pores are lined with an electrical conductor such as gold or platinum. The implant is surrounded by nutritive, insulated and protective protein-based gel such as sphingomyelin.

The above neural implant serves as an interface with the actual neurons of nerve fibers that have been severed, injured or otherwise damaged.

It is, accordingly, an object of the present invention to provide a prosthetic axon or, more simply, a synthetic pulse carrier capable of bridging a damaged area of the nervous system in order to thereby allow substantially normal passage of bioelectrical impulses therethrough.

It is a further object to provide a biologically compatible micro-electronic semi-conductor chip suitable for implantation at the damaged interface of nerve fibers.

The above and other objects and advantages of the present invention will become apparent from the hereinafter set forth Detailed Description of the Invention, the Drawings and appended Claims.

DETAILED DESCRIPTION OF THE INVENTION

Figure 1:
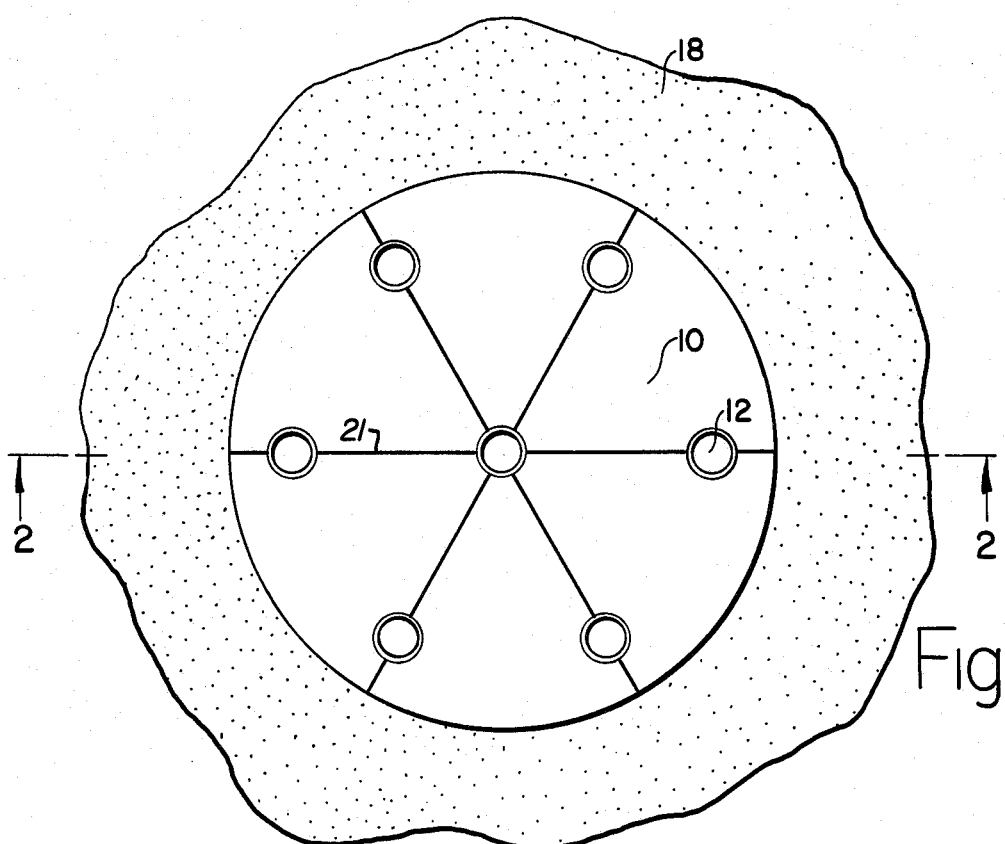
FIG. 1 is an equatorial cross-sectional schematic view of the present inventive implant.
Figure 2:
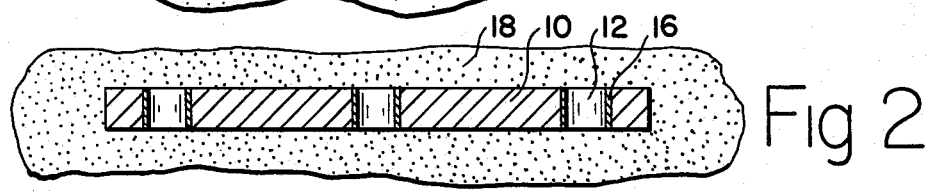
FIG. 2 is a horizontal cross-sectional view through the center of the semi-conductive disc taken along line 2—2 of FIG. 1.

With reference to FIG. 1, there is shown a semi-conductive disc 10 which, in a preferred embodiment, is formed of silicon. The diameter of said disc is in the range of 0.25 mm to 25 mm. Provided therein is a plurality of pores 12, which pores may include a spectrum of different diameters in the range of 100 microns to 2.5 mm, such diameters selected to conform to the diameters of nerves to be prosthetically bridged.

Monocrystalline silicon is preferred, although polycrystalline may be used as the semi-conductive disc 10. It is processed via "float-zone" techniques following "seed-crystal" implantation. Silicon is highly suitable in that it is not oxidized to any great degree by the human body, nor is it affected by the body's basic saline fluid properties. The implant disc is thus a semiconductor adapted to prevent neural interaction which may be deemed unfavorable. For example, singular neural connections are not a problem. In areas of neural bundles, ganglions, plexuses and the central nervous system, afferent and efferent nerve fibers when joined using the same disc must not act electrically or chemically upon one another. The semi-conductive medium (silicon) acts to minimize this effect.

Various substances implanted in Charles River strain rodents have shown silicon to be superior when nerve conductivity over severed peripheral nerves was tested. The size of the disc may vary according to the size or diameter(s) of the severed nerve or nerves.

The pore size must match the nerve diameter size for maximum efficiency of conductivity, and healing of the nerve endings. Like fracture healing, close proximity of the nerve endings will enhance neural performance.

Figure 3:
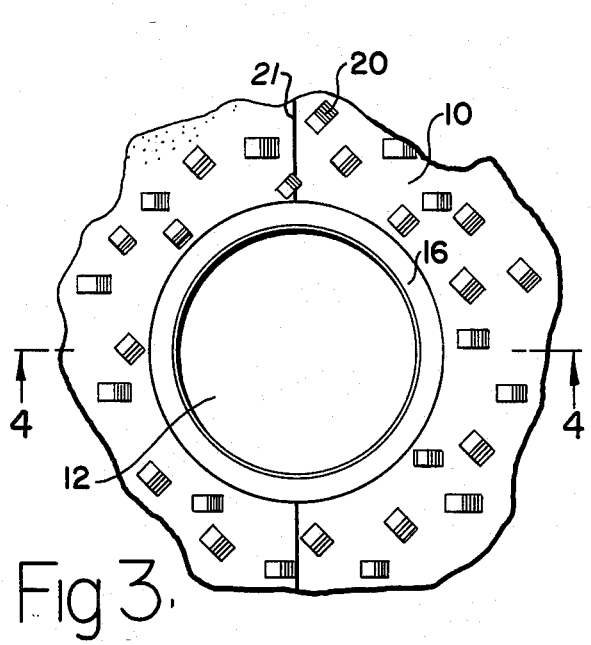
FIG. 3 is an enlarged view of a single pore of the semiconductive disc.
Figure 4:
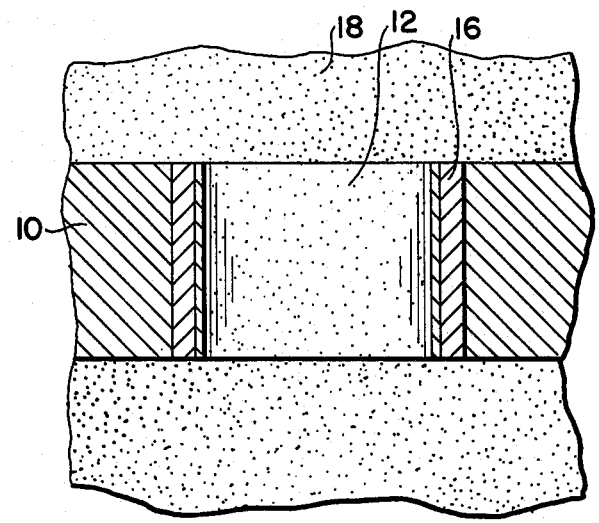
FIG. 4 is a vertical cross-sectional view of a single pore taken along line 4—4 of FIG. 3.

As shown in FIGS. 3 and 4, the inner cylindrical surface of each pore 12 is covered by an electrical conductor 16 such as gold or platinum. This configuration permits electrical conduction of bio-electrical signals through the conductor 16, while permitting suitable tissue growth through the plurality of pores 12.

The implant is surrounded by a nutritive and protective protein-phospholipid gel 18 such as spingomyelin, which gel also entends into the pores 12.

The protein-gel is a synthetic organic protein which resembles a lecithin-type compound whose formula or composition is different from the prior art of Richter Et Al (see Background of the Invention) in the use of a protein gel.

The disc 10 can be bonded to the protein gel 18 using methods disclosed in U.S. Pat. No. 4,307,472 to Morris, which relates to the bonding of semi-conductive materials to porous polymeric materials.

In addition, a porous coating and hydrophilic polymer may be applied to gel 18 in order to minimize fibrosis of surrounding tissues and to encourage normal circulatory and electrolite flow in the neighborhood of the implant.

The gel 18 is a protein-phospholipid material which, in preferred embodiment, is an amidomyelin ($C_{44}H_{92}N_2PO_{10}$) which is an organically synthesized monoaminomonophosphatided. This is a lipoid containing a phospatide having an atom of nitrogen and an atom of phosphorus per molecule. The phospatide is a fatty acid ester of phosphorilated polyvalent alcohol. It has been found that a gel of the above composition provides for insulation of the disc 10 and support at the time of implantation, in the general area, and tissue support as the area of surgery heals.

The above neural implant may be applied to the peripheral as well as to the central nervous system. This is due to the fact that the present prosthetic axon forms a new synapse or synaptic junction regardless of the group of nerve fibers with which it is interfaced.

With respect to specifications of specific implants, the size of the implant will vary with the area of nerve damage with which the implant is to be used. Sterility can be assured through the use of conventional sterilizing agents such as ethylene oxide or gamma radiation.

The silicon disc itself can be formed of a purified hi-grade silicon wafer, preferrably circular in shape and having a thickness of between 0.5 and 2.0 mm.

In addition, since nerve impulses are carried via combination of chemical and electrical impulses, the silicon may be doped with elements such as phosphorous and boron to cause the silicon chip to exhibit electrical properties such as dual axial polarity and static charge to enhance neural transmission in specific areas of the nervous system.

The electrical conductor 16 of the pores 12 is formed of high quality gold (0.999 fine) or high quality platinum (0.999 fine). A possible additive to these metals may comprise a small percentage of iridium.

The conductive coating 16 must be capable of interfaceing with the mamalian nervous system and therefore must contain gold in that gold is the most biocompatible metal available. The gold is deposited with sufficient surface energy to enhance nucleation and produce a micro-rough surface.

This surface tends to reduce the magnitude of the electrocyte impedance to 340 micro-ohms per square micro-meter at one kilohertz. Neural activity consists of 251 micro-second duration current pulses, or axion currents, flowing through active cell membranes into extracellur spaces surrounding axions and cell bodies in the nervous system.

The radial thickness of the conductor 16 will be determined by the micro-voltage potential of the damaged nerve fibers as determined by pre-testing of the nerve via electromyelograph (EMG) procedures. Higher density test results will call for an increased electrical resistance of the conductor 16, while lower density nerve readings will call for a lower density. This measuring of the electrical resistance of the damaged nerve is necessary in order to assure the best possible conductive match between the conductor 16 and the damaged nerves.

The size of the pores 12 will vary according to the diameter of the injured nerve area. The range in pore size will be from 100 microns up to 2.5 mm. Pores may be singular, a plurality, or a multiplicity and may be provided in a range of diameters.

The pores are not closer than 100 microns to one another, to reduce non-compatible nerve interaction. This is critical to normalizing nerve flow due to the current density at the active membrane which is $0.01A/CM^2$. Axon currents create potential gradients or axon potentials which are easily disrupted or shorted-out by cross conductivity reactions. Therefore, a 100 micron separation is necessary between pores.

It is noted that the silicon disc 10 is non-porous, but the surface thereof may be convoluted or laser ridged as shown at 10 in FIG. 3, and may also be micropored in order to assist in tissue adhesion, fluid flow, and adhesion of the gel 18 to the disc 10 during the early period following implantation. Linear furrows 21 may also be laser formed. Such furrows will facilitate removal of the disc 10, if necessary, after surgery.

In addition, the impedance match between the present neural implant and the damaged nerve fibers may be improved by incorporating a network of impedance microcircuitry onto the surfaces of disc 10 and between the pores 12. Such an impedance network may be formed utilizing the methods of what is termed Simose technology, incorporating a network of impedance microcircuitry. This circuitry, within conductor 16, as with the circuitry in disc 10, may be calibrated through the use of EPROM technology within the microcircuitry. More particularly, the impedance circuitry contained on the disc/chip and within the pores is a programmable chip designed to contact the gold conductor and act as a pre-programmed potentiometer to regulate neural flow.

The impedance circuitry is programmed by state-of-the-art EPROM Technology. The impedance circuitry is composed of gallium arsenide coated with a hydrophilic polymer, to help minimize fibrosis. Gallium arsenide chips can operate at 10 time higher frequency and five times faster than prior art silicon microcircuits. This is critical in interpretation of the intricate neural impulses.

The range of programmobility of the above-referenced EPROM is between 34 and 3400 micro-ohms per square micrometer. The programming of the EPROM will typically occur during surgery.

Figure 5:
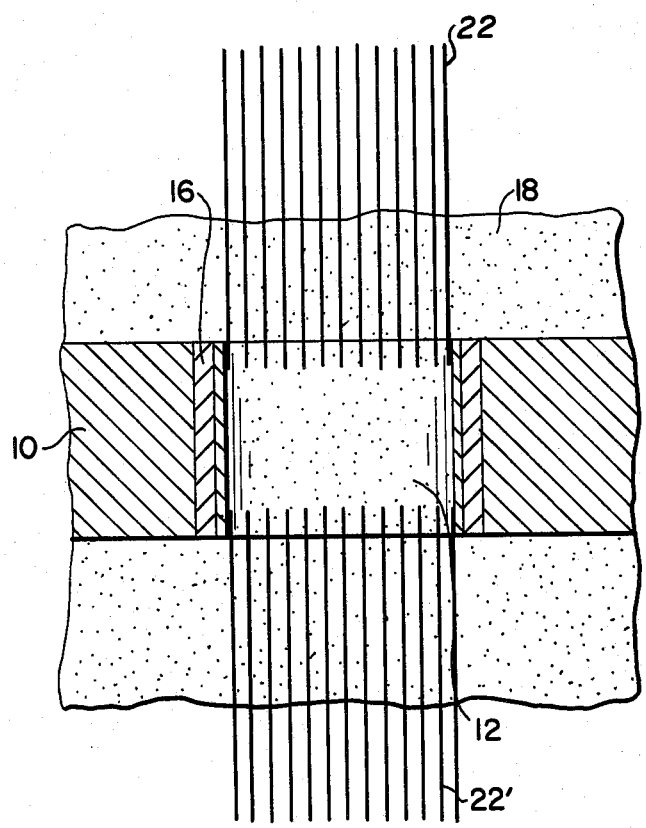
FIG. 5 is a schematic view, similar to FIG. 4, showing the implantation of nerve fibers into the gel of the implant.

With reference to FIG. 5, the embedding of nerve fibers 22 and 22' is shown into gel 18 which gel extends into the pores 12 and abuts conductor 16. Conduction of the biochemical pulses of the nervous system then occurs across the equatorial center of each pore 12.

The use of silicon, gold, and protein gel will minimize the formation of fibroplasts within the pores. Although some fibrosis is unavoidable, the diameter of the disc and pore size, as above set forth, is critical in preventing fibrosis. Pore sizes will vary with nerve diameter but should allow 10 to 100 micron clearance, depending on nerve location, to prevent occlusion by connective tissue. However, a smaller clearance will favor maximum nerve regeneration.

The nerve endings are attached to the disc by first inserting medical silastic tubing into the pores and micro-suturing the proximal and distal nerve endings to the silastic. This method is helpful in preventing compression of the axons against the disc, reducing stress, and preventing movement of the nerve endings. Nerve endings normally fill the cross-section of the silastic. The silastic size would be 3 to 6 mm in length, but pore size in width. Medical silastic is strong, flexible, does not calcify over extended periods, does not degrade, and exhibits excellent biocompatibility.

The prosthetic axons, after curing the silastic insert for 45 minutes at 140° C., is rinsed in de-ionized water, sterilized (autoclave or ethylene oxide), and packaged in physiological saline.

The prosthetic axon is implanted by resecting back 2 mm of the nerve epineurium from the severed nerve ends. The implant is placed between mattress sutures placed at either end. The sutures pass through the epineurium, secure the nerve endings to the silastic, and approximate the two endings within the pore of the silicon disc. This procedure insures that the perineurium of the nerve will remain intact. A nylon suture knot remains outside the silastic, reducing stress within the tube. This procedure is accomplished microsurgically.

After implantation, EMG testing and galvanic stimulation may be used in order to check and/or stimulate the patient's progress. Also, it is noted that follow-up injections of protein gel may be necessary to enhance the healing process.

The prosthetic axon will encourage regeneration of peripheral nerves. With continued research and development of the impedance circuitry (gallium arsenide chips), the electronic interpretation of neural impulses can be applied directly to the central nervous system.

Accordingly, while there have been shown and described the preferred embodiment of the present invention, it will be understood that the invention may be embodied otherwise than as herein specifically illustrated or described and that within said embodiments certain changes in the detail and construction, and the form of arrangement of the parts may be made without departing from the underlying idea or principles of this invention within the scope of the appended claims.

I claim:

1. A prosthetic axon for electrically bridging damaged nerve fibers, comprising:
   (a) a semi-conductive disc having therein a plurality of pores substantially parallel to the polar axis of said disc, said pores having an interior coating of electrically conductive material extending substantially from the top to bottom surfaces of said disc; and
   (b) a protein gel within which said semi-conductive disc is embedded, and into which respective sides of said damaged nerve fibers are secured at opposing sides of opposite pore ends of said disc, said gel in electrical contact with said conductive interior material of each of said plurality of pores.

2. The prosthetic axon as recited in claim 1 in which said protein gel comprises a phospholipid gel.

3. The prosthetic axon as recited in claim 2 in which said phospholipid gel comprises spingomyelin.

4. The prosthetic axon as recited in claim 1 in which the maximum diameter of said disc is in the range of 0.25 to 25 mm.

5. The prosthetic axon as recited in claim 4 in which the diameters of said pores is in the range of 100 microns to 2.5 millimeters, such diameters selected to conform to the diameters of the nerves to be prosthetically bridged.

6. The prosthetic axon as recited in claim 5, further comprising:
   a hydrophilic polymer bonded to said protein gel, thereby minimizing fibrosis of surrounding tissue and encouraging normalizing circulatory and electrolyte flow across the prosthetic axon.

7. The prosthetic axon as recited in claim 1 in which at least one surface of said disc further comprises an impedance network disposed thereon,
   whereby impedance matching between the damaged sides of the nerve fibers is thereby enhanced.

8. The prosthetic axon as recited in claim 7 in which said impedance network is embedded both (i) within said conductive coatings of said pores and (ii) on said disc between said conductive pore coatings,
   whereby intrapore and interpore impedances respectively between damaged nerve ending and between separate nerves within nerve bundles are therein matched.

9. The prosthetic axon as recited in claim 7 in which said impedance network includes programmable calibration means.

10. The prosthetic axon as recited in claim 9 in which said programmable calibration means comprises an EPROM chip.

11. The prosthetic axon as recited in claim 7 in which said semi-conductive disc is selectively doped to control its axial polarity and static electrical properties.

12. The prosthetic axon as recited in claim 7, further comprising bonded silastic medical tubing to each pore for holding the proximal and distal nerve endings therein in a stress-free manner, prior to micro-suturing of the nerve endings into each pore and to its corresponding pore coating.

13. The prosthetic axon recited in claim 7 in which said semi-conductive disc comprises a silicon disc.

14. The prosthetic axon as recited in claim 7 in which said electrically conductive interior coating of said pores is selected from the group consisting of gold, platinum, iridium, or any combination thereof.

15. The prosthetic axon as recited in claim 7 in which the surfaces of said disc are convoluted.

16. The prosthetic axon as recited in claim 7 in which the surfaces of said disc are ridged.

17. The prosthetic axon as recited in claim 7 in which the surfaces of said disc are micropored.

* * * * *